US009045565B2

(12) United States Patent
Ritter et al.

(10) Patent No.: US 9,045,565 B2
(45) Date of Patent: Jun. 2, 2015

(54) WATER-SOLUBLE POLYSACCHARIDE ETHERS AND THEIR USE

(75) Inventors: Helmut Ritter, Wuppertal (DE); Bernd Mueller, Augsburg (DE); Dirk-Henning Menz, Diedorf (DE)

(73) Assignee: PHARMPUR GMBH, Koenigsbrunn (DE)

( * ) Notice: Subject to any disclaimer, the term of this patent is extended or adjusted under 35 U.S.C. 154(b) by 176 days.

(21) Appl. No.: 13/390,733

(22) PCT Filed: Aug. 17, 2010

(86) PCT No.: PCT/EP2010/061971
§ 371 (c)(1),
(2), (4) Date: May 4, 2012

(87) PCT Pub. No.: WO2011/020829
PCT Pub. Date: Feb. 24, 2011

(65) Prior Publication Data
US 2012/0238524 A1    Sep. 20, 2012

(30) Foreign Application Priority Data

Aug. 17, 2009    (DE) .......................... 10 2009 037 514

(51) Int. Cl.
| | |
|---|---|
| C08B 13/00 | (2006.01) |
| A61L 27/20 | (2006.01) |
| C08B 11/20 | (2006.01) |
| C08L 1/32 | (2006.01) |
| C09K 19/36 | (2006.01) |
| C09K 19/38 | (2006.01) |
| C08B 15/00 | (2006.01) |
| A61K 9/00 | (2006.01) |

(52) U.S. Cl.
CPC ................. *C08B 13/00* (2013.01); *C08B 15/00* (2013.01); *A61K 9/0051* (2013.01); *A61L 27/20* (2013.01); *C08B 11/20* (2013.01); *C08L 1/32* (2013.01); *C09K 19/36* (2013.01); *C09K 19/3819* (2013.01)

(58) Field of Classification Search
None
See application file for complete search history.

(56) References Cited

U.S. PATENT DOCUMENTS

| | | | |
|---|---|---|---|
| 4,764,360 A | 8/1988 | Mälson | |
| 5,422,376 A | 6/1995 | Webb | |
| 7,585,983 B2 | 9/2009 | Reuter et al. | |
| 7,618,619 B2 | 11/2009 | Melles | |
| 2003/0088233 A1 | 5/2003 | Melles | |
| 2004/0227128 A1 | 11/2004 | Reuter et al. | |

FOREIGN PATENT DOCUMENTS

| | | |
|---|---|---|
| EP | 1263363 A1 | 12/2002 |
| EP | 1440974 A2 | 7/2004 |
| WO | 8602548 A1 | 5/1986 |
| WO | 01/66053 | 9/2001 |
| WO | 2008035372 | 7/2007 |

OTHER PUBLICATIONS

Singh, S. (2002).Chapter 1—Liquid crystals: fundamentals. World Scientific.*
Knill, C. J., & Kennedy, J. F. (2005). Chapter 41—Cellulosic biomass-derived products. In: Polysaccharides: structural diversity and functional versatility. Marcel and Dekker, New York, 937-956.*
Hu, T., Yi, J., Xiao, J., & Zhang, H. (2010). Effect of flexible spacer length on the mesophase structures of main-chain/side-chain liquid crystalline polymers based on ethyl cellulose. Polymer journal, 42(9), 752-758.*
Yang, L., Kuang, J., Li, Z., Zhang, B., Cai, X., & Zhang, L. M. (2008). Amphiphilic cholesteryl-bearing carboxymethylcellulose derivatives: self-assembly and rheological behaviour in aqueous solution. Cellulose, 15(5), 659-669.*
Roman, M., Dong, S. P., Hirani, A., & Lee, Y. W. (2009). Cellulose nanocrystals for drug delivery. Polysaccharide Materials: Performance by Design, American Chemical Society, Washington DC, 81-91.*
Eng translation of Written Opinion dated Feb. 17, 2012 for PCTEP/2010/061971, filed Aug. 17, 2010.
Eng translation of International Preliminary Report on Patentability dated Feb. 21, 2012 for PCTEP/2010/061971, filed Aug. 17, 2010.
Changcheng Wu et al, XP-001125791, "The Synthesis and thermotropic liquid crystalline behavior of mesogenic moiety-linked ethyl cellulose", Polymer Bulletin, vol. 48, pp. 33-41 (2002).
X. Hu et al, XP004549801, "Preparation, characterization and novel photoregulated rheological properties of azobenzene functionalized cellulose derivatives and their α-CD complexes", J. Polymer, vol. 45, No. 18, (2004), pp. 6219-6225.
Weiyan Wang, XP019539832, "Effect of α-Cyclodextrin on the Photoisomerization of Azobenzene Functionalized Hydroxypropyl Methylcellulose in Aqueous Solution", Polymer Bulletin, vol. 59, No. 4, (2007), pp. 537-544.

(Continued)

*Primary Examiner* — Shaojia Anna Jiang
*Assistant Examiner* — Dale R Miller
(74) *Attorney, Agent, or Firm* — Fleit Gibbons Gutman Bongini & Bianco PL; Martin Fleit; Paul D. Bianco

(57) ABSTRACT

The invention relates to modified polysaccharide ethers having a weight-averaged molecular weight of 40,000 to 500,000 g/mole, zero shear viscosity of more than 10 Pa·s, and pseudo-plasticity of more than 20. These modified polysaccharide ethers are obtainable by reacting cellulose-based polysaccharide ether(s) with at least one mesogenic modification agent or modified polysaccharide ethers, obtainable by reacting polysaccharide ether(s) selected from hydroxypropylmethyl cellulose (HPMC), hydroxyethylmethyl cellulose (HEMC), methyl cellulose, and cellulose ethers with methyl and/or ethyl and/or propyl groups and mixtures thereof, with at least one mesogenic modification agent. These substances can be used to produce gel-like to stable aqueous preparations having viscoelastic flow properties, which are suited for use in the human body, particularly within the scope of ophthalmologic procedures.

20 Claims, No Drawings

(56) References Cited

OTHER PUBLICATIONS

Tianhui Hu et al, XP-002606671, "Design, synthesis, and characterization of a combined main-chain/side-chain liquid-crystalline polymer based on ethyl cellulose", Cellulose, vol. 17, No. 3, (2010) pp. 547-558 (2010).

ChangCheng Wu et al, XP-001161609, "The synthesis and thermotropic behaviour of an ethyl cellulose derivative containing azobenzene-based mesogenic moieties", Liquid Crystals, vol. 30, No. 6, pp. 733-737, (2003).

V.A.E. Shaikah et al, XP002606667, "Thermotropic Behavior of Cholesterol-Linked Polysaccharides", Journal of Applied Polymer Science, vol. 70, No. 1, pp. 195-201, (1998).

V.A.E. Shaikah et al, XP002606668, "Thermotropic Liquid Crystalline Behavior of Cholesterol-Linked Hydroxyethyl Cellulose", Journal of Applied Polymer Science, vol. 72, No. 6, pp. 763-770, (1999).

V.A.E. Shaikah et al, XP002606669, "Thermotropic Behavior of Lithocholic Acid Derivative Linked Hydroxyethyl Cellulose", Journal of Applied Polymer Science, vol. 100, No. 3, pp. 1995-2001(2006).

Jang Hoon Kim et al, XP-02606670, "Synthesis and Characteristics of Hydxoxypropyl Celluloses Containing Cholesteryl and Acryloyl Groups", Polymer Korea, vol. 28, No. 1, pp. 92-102 (2004).

International Search Report, published Feb. 24, 2011 for PCTEP/2010/061971.

Written Opinion for PCTEP/2010/061971, filed Aug. 17, 2010.

Steve A. Arshinoff,MD et al, "Laboratory Science New classification of ophthalmic viscosurgical devices"—2005, pp. 2167-2171, vol. 31 Nov. 2005, Elsevier Inc.

* cited by examiner

WATER-SOLUBLE POLYSACCHARIDE ETHERS AND THEIR USE

FIELD OF THE INVENTION

The invention concerns novel polysaccharide ethers with mesogenic side groups and the aqueous solutions of such substances and their use for the production of gel-like to stable aqueous preparations with viscoelastic flow properties, which are suitable for use in the human body, in particular, within the scope of ophthalmological interventions.

BACKGROUND OF THE INVENTION

The use of so-called ophthalmological viscoelastic devices (OVDs) in ophthalmological interventions for the protection of tissues and implants and for the reduction of mechanical forces, which can lead to damage during the preparation and execution of an operative or diagnostic intervention, has been known for many years. These OVDs are as a rule aqueous polymer solutions that are adapted to the conditions of the human eye by adjustment of a specific pH value and a specific osmolarity (adjustment of the polymer-dependent, colloid-osmotic pressure as well as the osmotic pressure that is determined by the contained inorganic salts). In particular, hyaluronic acid and its physiologically compatible salts, chondroitin sulfate, and hydroxypropyl methylcellulose are known as base polymers for these preparations.

A frequent use of these substances is to be found in the fact that in a cataract operation—that is when replacing the natural eye lens—the eye chamber and the capsular bag between the removal of the natural lens and the implantation of the artificial new lens are filled with the viscoelastic device, so as to avoid a collapse of this cavity. At the same time, the viscoelastic devices protect the affected tissues and support the sliding capacity of the instruments and implants used. In the further course of the operation, the viscoelastic devices must then be removed.

As a result of this circumstance, it is necessary that opthalmological viscoelastic devices have the following flow properties: in the absence of shear forces, dimensionally stable gels must form; otherwise, it must be possible to readily inject and aspirate them through a syringe needle. An appropriate flow property is very well approximated by solutions of hyaluronic acid and its salts. Hyaluronic acid is a naturally occurring biopolymer from the group of glucose aminoglucans. Although the substance is widely dispersed, it is nevertheless cost-intensive to tap productive sources for high molecular weight hyaluronic acid. For the most part, this is done by two methods—namely, the extraction from animal tissues or by a fermentation production. The products from animal sources surpass the fermentation-produced products as a rule in the characteristics dependent on the molecular weight. Thus, starting products of commercially available products with particularly high zero-shear viscosities are mostly of animal origin and exhibit an average molecular weight of 4 million daltons. The fermentation-produced products have a molecular weight of approximately 2.5 million daltons and correspondingly low zero-shear viscosities. The use of products of animal origin is connected with the risk of a BSE/TSE transmission. Furthermore, their use as well as the use of fermentation-produced products requires a strict control of the endotoxin content, since endotoxins can contaminate the product during production.

Hyaluronic salt solutions are not only used in ophthalmology, but rather also in rheumatology and orthopedics—for example, arthrosis treatment. On the one hand, by replenishing the synovial fluid, the sliding capacity of the cartilage and the absorption of abruptly acting forces can be improved; on the other hand, inflammation-inhibiting effects are discussed. Also, uses in dermatology and plastic surgery, for example, for injection under wrinkles, have found large proliferation.

Although hyaluronic acid salt solutions exhibit good technical properties and aside from the aforementioned uses, have captured additional usage areas in medicine, there is nevertheless a need to obtain corresponding products from simpler, more easily accessible and less cost-intensive sources. Thus, in the international application, WO2008/035372, Reliance Life Sciences Pvt. Ltd., the proposal is made to obtain hyaluronic acid from bacteria. These fermentation-obtained products, however, have limited rheological properties due to their lower molecular weight, in comparison with hyaluronates from higher organisms. Furthermore, the bacterially produced hyaluronic acid is subject to the main disadvantage of this class of substances, which consists in that the aqueous solutions are thermally sensitive and therefore must be cooled during storage and transport. Furthermore, the preparations specimens lose considerably in viscosity in a steam sterilization due to a reduction of the molecular weight. It is particularly the viscosity in solution, however, which is the decisive technical characteristic of the products, so that an obvious disadvantage is present here.

Thus, there has not been a lack of attempts to use synthetic polysaccharide ethers, such as hydroxypropyl methylcellulose, for this use. Thus, U.S. Pat. No. 5,422,376, Dow Chemical, proposes the synthesis of a viscoelastic material based on a hydroxypropyl methylcellulose with a molecular weight between 375,000 and 420,000 daltons. Hydroxypropyl methylcellulose (HPMC) has proved to be excellent with respect to body tolerance and can be easily obtained from cellulose raw materials, as they extensively exist in nature. The disadvantage, however, is that the viscosity of aqueous preparations is not dependent on shear force in the manner in which this is known from hyaluronic acid. Stable HPMC solutions can therefore not be metered simply through a syringe needle. Furthermore, to attain high zero-shear viscosities, such high concentrations would be required that compatible osmolalities could not be maintained.

SUMMARY OF THE INVENTION

In view of the background of this state of the art, the inventors have taken up the task of preparing polysaccharide ethers that can be produced from readily accessible raw materials whose aqueous solutions under shearing effects exhibit flow properties similar to those of hyaluronic acid salt solutions, that with common steam sterilization methods, do not experience any substantial viscosity reduction and that can be stored and transported without cooling, without experiencing any quality loss. At the same time, in particular, the application-related characteristics of pseudo-plasticity and dispersivity should, in case of high zero-shear viscosities, be adapted to the clinical requirements (Steve A. Arshinoff, Masoud Jafari; J. Cataract Refract. Surgery, Vol. 31, 2005, 2167-2171, and B. Dick, O. Schwenn, N. Pfeiffer; Ophthalmologe, 1999, 193-211).

The object of the invention thus refers to water-soluble polysaccharide ethers, in particular, with the capacity for aggregate formation in aqueous solution, namely, modified polysaccharide ethers with a weight-averaged molecular weight of 40,000-500,000 g/mol, a zero-shear viscosity of more than 10 Pa·s and a pseudoplasticity of more than 20, which can be obtained by a reaction of polysaccharide ether(s) based on cellulose with at least one mesogenic modification agent or modified polysaccharide ethers, which can be obtained by a reaction of polysaccharide ether(s) selected from hydroxypropyl methylcellulose (HPMC), hydroxyethyl methylcellulose (HEMC), methylcellulose, cellulose ethers with methyl and/or ethyl and/or propyl groups and mixtures thereof, with at least one mesogenic modification agent.

Another object of the invention refers to generic products whose solutions are permanently colored or attain a polyelectrolyte character by additional substituents.

Moreover, viscoelastic preparations for injection into the human body are also an object of the invention; they contain one of the modified polysaccharides, or a mixture thereof with themselves or other OVD, in particular, hyaluronic acid, as well as physiologically acceptable salts and/or a buffer system and, if desired, other active substances and/or auxiliaries in aqueous solution.

The surprising flow properties, which the products in accordance with the invention exhibit in aqueous solution, could not be predicted by any scientific theory. In particular, the specialist had not expected viscoelastic properties to be imparted to polysaccharide ethers by a modification with mesogenic groups, in particular, cholesteryl side groups, which are otherwise known only from aqueous solutions of hyaluronic acid. Explanation attempts are based on the fact that polysaccharide ethers, for example, hydroxypropyl methylcellulose, form star-shaped fringe micelles in aqueous solution. It is therefore suspected that the mesogenic groups lead to an increased aggregation of these fringe micelles. Surprisingly, the interactive forces involved thereby are of such a nature that finally, the rheological behavior of hyaluronic acid solutions is attained without their temperature sensitivity appearing.

DETAILED DESCRIPTION OF THE INVENTION

In a very general embodiment, the invention concerns water-soluble polysaccharide ethers, which were subjected to another modification step for the introduction of mesogenic groups. Water-soluble, in the sense of the invention, are polysaccharide ethers that at least with concentrations below 10 wt % and temperatures below 40° C. form clear, transparent solutions or gels. The polysaccharide ethers can thereby be derived from any polysaccharides. According to a preferred embodiment of the invention, the polysaccharides are derived from glucan. These are polysaccharides based on glucose. As preferred examples one can mention here glucans with $\alpha$-1,4-glycosidic bonding, such as $\alpha$-amylose, and glucans with $\beta$-1,4-glycosidic bonding, such as cellulose. Other glucans for this purpose are amylopectin, callose, or chitosan (partially deacetylated chitin). Another polysaccharide is polygalactomannan, which is usually obtained from guar gum or from locust bean gum. Other polysaccharides for this purpose are dextran, xanthan, and alginates.

The polysaccharide ethers in accordance with the invention are etherification products of the aforementioned polysaccharides. As etherification agents, the usual etherification agents used on a large scale are used here. These are halogen alkanes with preferably 1-3, but mostly no more than 6 C atoms or epoxides, such as ethylene oxide or propylene oxide, or their higher homologs (for example, with up to 7 C atoms), such as 1-olefin oxides. Technically common is the use of methyl chloride, ethyl chloride, individually or together with one or both of the aforementioned epoxides. Known products produced on a large scale are methylcellulose, ethylcellulose, hydroxyethylcellulose, hydroxypropylcellulose, and analogue starch derivatives. Known and common are also mixed forms, such as hydroxyethyl methylcellulose, hydroxypropyl methylcellulose, and analogue starch products. Another important class of substances involves the etherification products of cellulose, starch, or other polysaccharides with chloroacetic acid. In this way products such as carboxymethylcellulose and carboxymethyl starch are formed. Such functionalized polysaccharide ethers can carry other substituents, such as methyl or hydroxyethyl or hydroxypropyl groups.

For the technical characteristics of the polysaccharide ethers, which are described here as starting substances of the modified polysaccharide ethers substituted in accordance with the invention, the degree of substitution is important. This indicates how many substituents are present on average per monomer component. In the case of the cellulose, the monomer component is the anhydroglucose unit. This has three free OH groups. From this it is clear that for alkyl substituents or for the carboxymethyl group, the theoretical maximum degree of substitution is 3. This is, however, never attained technically. For practical use, the degrees of substitution are between 0.1 and 2.5.

In the case of modification with ethylene oxide or propylene oxide, a new free OH group is formed from a free OH group of the macromolecule. Therefore, with a substitution with ethylene oxide or propylene oxide, an apparent degree of substitution >3 can also be established. In practice this means that an anhydroglucose unit with more than 3 molecules ethylene oxide or propylene oxide is substituted. These molecules, however, are not necessarily deposited directly on the anhydroglucose ring, but rather oligoether or polyether side groups can also form, in that they are also deposited on the individually newly formed OH group.

Particularly preferred materials in the sense of the invention are derived from mixed polysaccharide ethers, such as from alkylhydroxy ethylcelluloses or alkylhydroxy propylcelluloses and analogue starch derivatives. Particularly preferred materials are hydroxypropyl methylcellulose and hydroxyethyl methylcellulose.

Ideal starting materials for the new polysaccharide ethers in accordance with the invention are alkylhydroxy ethylcelluloses or alkylhydroxy propylcelluloses, as they are offered by many manufacturers for pharmaceutical purposes. Among these, hydroxypropyl methylcellulose has found the most widespread use with regard to practical considerations. A particularly preferred starting material is a purified hydroxypropyl methylcellulose, as it is recommended as a synthetic viscoelastic material for ophthalmological uses and is described in U.S. Pat. No. 5,422,376, column 5, line 20 to column 6, line 64.

For the purposes of the invention under consideration here, what is generally valid is that such polysaccharide ethers that were produced in a heterogeneous phase are preferred. This is true for most technical products that are on the market. By production in a heterogeneous phase, the substitution of the OH groups on the polysaccharide molecule preferably takes place in the noncrystallized area (in the polymer-chemical sense). In this way, the products receive a kind of block copolymer structure—that is, in the originally noncrystalline area, there are more substituents than in the areas that, as crystallites, were reached only with difficulty by the alkylation agents during the production process. Without exact knowledge being available on this, it assumed that such a structure promotes the formation of the fringe micelles mentioned previously. Particularly preferred products in accordance with the invention form such fringe micelles in aqueous solution.

Outstanding starting materials for the modification described in the following are products with a degree of alkyl substitution between 0.5 and 2.3, in particular, between 1.0 and 2.0, and/or a degree of hydroxyalkyl substitution between 0.3-1.5. If both an alkyl substitution and a hydroxyalkyl substitution are present, then the degree of alkyl substitution should be 0.8-2.2, preferably 1.0-2.0, and simultaneously, the degree of hydroxyalkyl substitution, 0.05-1.0, preferably 0.1-0.3. The specialist will rather select medium to higher degrees of substitution with cellulose ethers; with starch ethers, he will rather select lower degrees of substitution.

The molecular weight of the preparation in accordance with the invention can be selected by the specialist within broad limits. It generally is determined by the natural source for the polysaccharide. Since the viscosity of the preparation is a decisive parameter, it is advantageous to select products with the highest possible molecular weight. The usual average molecular weights for cellulose ethers lie between 10,000 and 500,000 daltons. When they are described in this application, we are dealing with the weight average.

In accordance with the invention the polysaccharide ethers are modified by the introduction of a mesogenic group. The term mesogenic group is known to the specialist. It is understood to mean all groups or substances that are suitable for forming mesophases in a certain temperature range—that is, phases with a higher state of order than in isotropic liquids, but with a lower one than in crystal lattices. Such phases exhibit the optical anisotropy of crystals and the mobility of absolutely isotropic liquids. Mesophases are also called liquid-crystalline phases or anisotropic liquids.

The mesogenic group can, within the scope of the invention, be one that is suitable for the formation of smectic, nematic, or cholesteric liquid-crystalline phases. They can thus be rod-shaped, disk-shaped (discotic) or cholesteric mesogenic groups.

Numerous liquid-crystalline (mesogenic) compounds that have functional groups and can be bound in a simple manner are available to the chemist active in the field of liquid-crystalline compounds.

A large number of suitable aromatic and aliphatic mesogenic substances are described in European Patent Application No. EP 1440974 as radical M (mesogenic radical), in Sections 19-28. Reference is hereby made explicitly to this publication.

In accordance with the invention, the mesogenic groups are placed as a side chain of the polysaccharide molecule. The mesogenic structure can be bound directly on the chain, or via a shorter or longer intermediate group. As particularly preferred, in the sense of the invention, those mesogenic side groups that are strongly hydrophobic, have as low as possible a water solutbility, and/or are synthesized from more than 12, preferably more than 30, C atoms, can qualify. Thus, for example, side groups from the following starting molecules are suitable:
cholesteryl derivatives, such as:
cholesteryl chloroformate, cholesteryl hemisuccinate, cholesteryl chloride, cholesterol, cholestan-3-ol, and 5,6-dibromocholestan-3-ol.
cyclic terpenes, such as:
α-tocopherol, podocarpic acid, abietic acid, dehydroabietylamine.
steroids, such as:
hydrocortisone, β-sisosterol, 19-hydroxy-4-androstene-3, 17-dione, mestranol, stearyl glycyrrhetinate According to a preferred embodiment of the invention, cholesterol is introduced as the mesogenic group. Cholesterol or one of its derivatives has a OH group and can be bound to the polymer via a suitable difunctional intermediate group. The specialist can thereby attach the radical directly on the polymer chain, or via a longer intermediate group functioning as a spacer. For example, the direct bonding can take place via a carboxylic acid ester group. To this end, cholesterol is reacted with phosgene in the molar ratio 1:1 and the chloroformyl derivative thus produced is bound to the polymer, if desired, in the presence of basic catalysts or with the use of electromagnetic radiation, such as microwaves. In a similar manner, a bonding, however, can also take place via other difunctional groups—for example, via reactive compounds of dicarboxylic acids or via α-, Ω-dihalogen alkanes, diepoxides, or the like.

Synthetic mesogenic groups are suitable as additional or alternative mesogenic groups. They are anisotropic molecules, which mostly consist of a rigid aromatic system attached to flexible end groups. A large number of mesogenic groups that are also suitable for the invention under consideration here, and paths to their bonding on polymers are, for example, described in European Patent Application No. EP1440974. Particularly suitable here are fully synthetic mesognic/liquid-crystalline substituents, such as:
1-(4-trans-hexylcyclohexyl)-4-[2-(4-isothiocyanatophenyl)ethyl]benzene, 1-[4-(trans-4-heptylcyclohexyl)phenyl]-2-(trans-4-(4-isothiocyanatophenyl)cyclohexyl]ethane, 4-hexyl-4'-[2-(4-isothiocyanatophenyl)ethyl]-1,1'-biphenyl, 4-isothiocyanatophenyl-4-pentylbicyclo[2.2.2]octane-1-carboxylate, 4-[(S,S)-2,3-epoxyhexyloxy]phenyl-4-decyloxy) benzoate, 6-[4-(4-cyanophenyl)phenoxy]hexylmethacrylate, 4'-bromomethyl-2-biphenylcarbonitrile. Other suitable substances can be obtained in the chemicals market.

The degree of substitution of the water-soluble polysaccharide ethers in accordance with the invention with reference to the mesogenic groups is 0.0001-0.2, preferably 0.001-0.1. This means that on average per anhydroglucose unite 0.0001-0.2 or preferably 0.001-0.01 mesogenic groups are present.

According to another preferred embodiment of the invention, the polysaccharide ether in accordance with the invention contains other modifying side groups. Dye groups can be used as those other modifying side groups. A large number of dyes that can be bound to the OH groups of polysaccharides in a direct covalent manner are available to the organic chemist. The selection of a dye can therefore be based on the color hue on the one hand (light absorption), and on medicinal considerations. Dyes that have a sufficient biocompatibility and from which, for example, no allergenic potential is known, are therefore preferable.

The modification of the products in accordance with the invention can be required because of two reasons. On the one hand, the products in accordance with the invention are preferably used with operation techniques on the human eye and must with this use mostly be as quantitatively as possible removed at the end of the operation. To this end, it is helpful for the operator to recognize the product used by its color. Colored products are also helpful to control the protection of sensitive areas and to guide the use of viscoelastic devices in areas that are hard to delimit. Another reason is that with eye operations, incident or coupled radiation can be controlled (avoidance of light-induced damage of the retina) by means of colored material, in that the light of the used light source is at least proportionately absorbed by a colored material.

Depending on the desired application, the quantity of the dye is to be controlled. In the case where the dye is merely used for marking the viscoelastic liquids used, working with the lowest possible dyeing quantity with a high absorption power is preferable. According to a particularly preferred embodiment of the invention, fluorescent dyes can be used here, since the fluorescence radiation can be detected in a particularly easy manner. In actual practice, it has been demonstrated in particular that fluorescein derivatives are suitable—thus, for example, fluorescein derivatives with isothiocyanate groups that can be obtained on the market and to which polymers in accordance with the invention can be attached as carbamothioate.

When using dyes for the absorption of harmful quantities of light energy, higher degrees of substitution are required, which the specialist can determine directly from the required light absorption.

The specialist active in this area will, in particular, use reactive dyes for this application purpose, as they can be obtained on the market for the dyeing of cotton and other cellulose derivatives.

Reference is also made in this connection to international application WO86/02548, in which a dye that can be bound to a polysaccharide, in this case, dextran, is described. One advantage of the invention under consideration in comparison with this state of the art is to be found in the fact that in accordance with the invention, the dye is bound directly to the polymer underlying the viscoelastic material and not to another polymer that under certain conditions can behave differently, segregate, or be deposited on special cell systems, which is not desired here.

According to another embodiment of the invention, the products in accordance with the invention can also have a polyelectrolyte character. This can occur, for example, by the introduction of carboxymethyl groups.

In the modification of the polysaccharide ethers with the mesogenic substances and/or with the dyes, it has proved particularly preferable to work in a homogeneous solution. To this end, the cellulose ethers are dissolved in a solvent such as dimethyl sulfoxide or the like, and mixed with 0.1 mol % relative to the cellulose ether of an amine, for example, triethanolamine. The mesogen is then added, for example, in the form of cholesteryl chloroformate dissolved in a suitable solvent, or the dye in 0.1-molar sodium hydroxide, to the reaction medium. In order to provide for a better thorough mixing of the reaction medium, it has proved to be advantageous to stir this reaction mixture or also to process it in a kneader.

According to another embodiment of the invention, insoluble parts are separated, as is described in U.S. Pat. No. 5,422,376 cited in the beginning, so as to improve the characteristics of the viscoelastic preparations.

From the polysaccharide ether in accordance with the invention, it is possible in a simple manner to produce viscoelastic preparations, as they are used for ophthalmology. To this end, they are dissolved in aqueous salt solutions that perhaps also contain a suitable buffer. The quantity of polysaccharide ether to be dissolved is determined by the desired viscosity. It can be 0.05-5 wt %, preferably 1-3 wt %. Quantities of around 2 wt % have proved to be particularly favorable. The specialist can easily adapt the required concentration to the known application fields of hyaluronic acid preparations. The salts employed here are used to adjust the osmotic pressure. Suitable salts here are sodium chloride, potassium chloride, calcium chloride, and magnesium chloride, or other physiologically acceptable salts. The salt content is often below 1.5 wt %. In accordance with the invention, buffer systems are also added, preferably on the basis of sodium acetate and/or sodium citrate. With hydrochloric acid or sodium hydroxide, adjustment is made if required to a pH value between 5.5 and 8.5—for ophthalmological preparations, preferably between 6.8 and 8.1. As a rule, the total buffer quantity fluctuates thereby around or below 1 wt %. The osmolality is thus set between 200-400 milliosmol.

The preparations that are described in Sections 26-28 of European Patent No. EP1263363B1 can be regarded as an indication of a suitable viscoelastic solution.

In the production of the viscoelastic solution, care should also be taken that the molecular weight is not prematurely reduced by strong shear forces. It has therefore been shown that a preferred method is to isolate the prefinished solid polysaccharide ethers after the modification; if desired, to grind them; and then to disperse the solid preparation, if desired, according to a purification step for the separation of nondesired or disturbing lower-molecular admixtures in a non-solvent such as hot water; and subsequently, to convert the dispersion into a solution by cooling the aqueous bath, wherein a packing and sterilization step can follow.

The viscoelastic preparations in accordance with the invention are suitable for injection into the human body. One main application purpose is in the field of ophthalmology. There, the preparations can be used, for example, with cataract operations. In addition to this main usage area, the viscoelastic preparations in accordance with the invention, however, are also suitable auxiliaries in cosmetic surgery. Thus, similar to hyaluronic acid solutions, they can be used for injection of wrinkles in cosmetic treatments. Another usage possibility is in the field of orthopedics. There, the preparations can also be used, analogous to hyaluronic acid, as a supplement for the synovial fluid, for improvement of the viscous consistency, absorption of impact forces, and for improvement of the sliding capacity of cartilage and thus, the improved mobility of joints, and to this end are injected directly into the joint capsules. The products in accordance with the invention preferably exhibit a zero-shear viscosity >100 Pa·s; they can be sterilized with steam and can be stored and transported without cooling.

Preferred ranges for zero-shear viscosity are 10-20,000 Pa·s, preferably 10-10,000 Pa·s, more preferably 10-5000 Pa·s, even more preferably 10-1000 Pa·s. Other preferred ranges of zero-shear viscosity values are from 20-1000 Pa·s, more preferably 50-1000 Pa·s, even more preferably 100-1000 Pa·s, and even more preferably 500-1000 Pa·s.

Preferred ranges for the pseudo-plasticity of the products in accordance with the invention are 20-10,000, preferably 20-5000, more preferably 20-2000, even more preferably 20-1000. Additional preferred areas of pseudo-plasticity values are from 50-1000, more preferably 100-1000, even more preferably 200-1000, and even more preferably 400-1000.

Taking into consideration the structure of the individual cellulose derivative, the pseudo-plasticity correlates with the molecular weight.

Example 1

Derivatization of HPMC with Cholesteryl Chloroformate 5.0 g (24.7 mmol) dried HPMC and 554 mg (1.23 mmol) cholesteryl chloroformate were dissolved in 50 mL dry DMSO in a nitrogen atmosphere at 75° C. using a KPG stirrer. Subsequently, 345 µL (2.47 mmol) triethylamine were added and stirred at 75° C. for 16 h. The dissolved polymer was diluted with 50 mL DMSO and precipitated hot in a mixture of diethyl ether/ethanol (4:1). The solid was separated by filtration, washed with acetone, and subsequently extracted with acetone over 48 h. 5.1 g of a colorless solid were obtained (92% of the theoretical).

$^1$H-NMR (200 MHz, DMSO-d6, 100° C.): δ=4.54-4.26 (broad CH, 291H), 3.9-2.6 (wide multiplet), 1.13-1.00 (wide, —OCH$_2$CHOHCH$_3$ 225H), 0.91 (d, C$^{27}$H$_3$, 3H) 0.89-0.86 (m, C$^{19}$H$_3$, C$^{26}$H$_3$, C$^{28}$H$_3$, 9H), 0.69 (s, C$^{20}$H$_3$, 3H) ppm.

By the ratio of the integral of the C$^1$H signal of the glucoside and the C$^{20}$H$_3$ signal of the cholesteryl substituents, a degree of substitution of DS=1.15×10$^{-3}$ (≈0.74 wt %) resulted. The determination of the molecular weight gives a bimodal distribution with the two maxima at M$_1$=103,000 g/mol and at M$_2$=1,690,000 g/mol. These molecular weights do not represent the molecular weight of monodispersally dissolved chains. The specialist is aware that, in particular, hydrophobically modified cellulose ethers form aggregates that are partially or completely obtained under the measurement conditions used for the GPC measurements. The increase of the molecular weight can be correspondingly attributed to an increased aggregation. This limitation is valid for all experimentally determined molecular weights.

The 2 wt % solution in water had a turbidity temperature of 63.0° C., a zero viscosity of 1300 Pa·s, and a pseudo-plasticity of 229. The zero viscosity was increased by the factor 60 in comparison with the unmodified HPMC; the pseudo-plasticity, by the factor 10.

In accordance with a production method used in accordance with standards for pharmaceutical applications, a 2 wt % solution of the cholesteryl-modified HPMC in physiological buffer is used to fill 2.25 mL syringes and subsequently sterilized in a steam autoclave at 121° C. for 20 min. The zero viscosity of this solution declined thereby to 750 Pa·s; the pseudo-plasticity increased to 431. The zero viscosity of a comparison sample of hyaluronic acid (1.5 wt % in physiological buffer, zero viscosity η$_0$=640 Pa·s) declined to 8.3%.

All examples mentioned in the following are synthesized in accordance with the instructions mentioned above.

Example 2

Derivatization of HEMC with Cholesteryl Chloroformate $^1$H-NMR (200 MHz, DMSO-d6, 100° C.): δ=4.54-4.26 (broad C$^1$H, 281H), 3.9-2.6 (wide multiplet), 0.91 (d, C$^{27}$H$_3$, 3H), 0.89-0.86 (m, C$^{19}$H$_3$, C$^{26}$H$_3$, C$^{28}$H$_3$, 9H), 0.69 (s, C$^{20}$H$_3$, 3H) ppm.

By the ratio of the integral of the C$^1$H signal of the glucoside and the C$^{20}$H$_3$ signal of the cholesteryl substituent, a degree of substitution of DS=1.19×10$^{-3}$ (≈0.73 wt %) resulted. The determination of the molecular weight gave a trimodal distribution with the maxima at M$_1$=113,000 g/mol, M$_2$=438,000 g/mol and M$_3$=1,435,000 g/mol. The 2 wt % solution in water had a turbidity temperature of 60.3° C., a zero viscosity of 184 Pa·s, and a pseudo-plasticity of 356.

Example 3

Derivatization of HEMC with 4-(4-decyloxybenzoyloxy)benzoic acid chloride $^1$H-NMR (200 MHz, DMSO-d6, 100° C.): δ=5.63-5.33 (broad OH), 4.56-4.26 (broad C$^1$H), 4.0-2.6), (broad multiplet) ppm.

UV-Vis (H$_2$O); λ$_{max}$(A)=264 (0.573) nm

Via UV spectroscopy it is possible to determine the degree of substitution at DS=1.35×10$^{-3}$ (≈0.76 wt %) (ε$_{264\ nm}$=14,325 cm$^2$/mmol). The determination of the molecular weight gave a bimodal distribution with the maxima at M$_1$=242,000 g/mol and M$_2$=445,000 g/mol. The 2 wt % solution in water had a turbidity temperature of 61.7° C., a zero viscosity of 28.2 Pa·s and a pseudo-plasticity of 22.

Comparison Example 1

Derivatization of HPMC with Octyl Chloroformate

DS=2.56×10$^{-3}$ (≈0.63 wt %). The determination of the molecular weight gives a bimodal distribution with the two maxima at M$_1$=118,000 g/mol and at M$_2$=403,000 g/mol. The 2 wt % solution in water has a turbidity temperature of 68.3° C., a zero viscosity of 2.9 Pa·s, and a pseudo-plasticity of only 2.8.

$^1$H-NMR (200 MHz, DMSO-d6, 100° C.): δ=6.25-5.60 (broad OH), 4.54-4.26 (broad, C$^1$H, 130H), 3.9-2.7 (broad multiplet) 1.38-1.23 (m, C$^{3-7}$H$_2$, 10H), 1.13-1.00 (broad, —OCH$_2$CHOHCH$_3$, 92H) ppm.

By the ratio of the integral of the C$^1$H signal of the glucoside and the signal of the methylene groups C$^{3-7}$H$_2$ of the octyl substituent, the result is a degree of substitution of DS=2.56×10$^{-3}$ (≈0.63 wt %). The determination of the molecular weight gives a bimodal distribution with the two maxima at m$_1$=118,000 g/mol and at M=403,000 g/mol. The 2 wt % solution in water has a turbidity temperature of 68.3° C., a zero viscosity of 2.9 Pa·s, and a pseudo-plasticity of 2.8. The zero viscosity has sunk by the factor 10 in comparison with the unmodified HPMC.

Comparison Example 2

Derivatization of HPMC with Octadecyl Isocyanate (Hydrophobic Compound, but No Mesogen)

$^1$H-NMR (200 MHz, DMSO-d6, 100° C.): δ=5.95-5.30 (broad OH), 4.60-4.30 (broad, C$^1$H, 34.1H), 3.9-2.7 (broad multiplet) 1.51-1.43 (broad, C$^2$H$_2$, 2H), 1.40-1.25 (m, C$^{3-17}$H$_2$, 30H), 1.16-1.00 (broad, —OCH$_2$CHOHCH$_3$, 23.1H), 0.94-0.86 (broad, C$^{18}$H$_3$, 3H) ppm.

By the ratio of the integral of the C$^1$H signal of the glucoside and the signal of the methylene groups C$^{3-17}$H$_2$ of the octadecyl substituent, the result is a degree of substitution of DS=9.78×10$^{-3}$ (≈4.37 wt %). This modified polysaccharide ether is completely water-insoluble.

Analytical Methods:

Rheometry

Rheological measurements are carried out with a plate-plate structure (Sensor plate: PP35Ti; Measurement plate: MP35) on a Haake MarsII rheometer from the Fisher Scientific Company in a controlled stress mode. 2 wt % aqueous solutions are measured according to the European Norm EN ISO 15798:2001 for ophthalmological lubricants: Accordingly, the work is done at a temperature of 25+/−0.1° C. Dynamic viscosities are recorded in the range of γ̇=0.002-1000 s$^{-1}$. Zero viscosities are determined according to the Newton model in the range of γ̇=0.002-0.1 s$^{-1}$. The viscosity at γ̇=100 s$^{-1}$ was calculated according to the Ostwald de Waele model via the extrapolation of the power-law range of 10≤γ̇≤1000 s$^{-1}$. The pseudo-plasticity is produced by the ratio of the zero viscosity to the viscosity at γ̇=100 s$^{-1}$.

Turbidity Photometry 2 wt % solutions of the purified substance are measured in distilled water in a standard quartz glass cuvette. The measuring apparatus is a Tepper turbidity photometer with an LED light source (λ=592 nm).

UV-Vis Measurements

The measurements were carried out on a Nicolet UV 540 spectrometer. Data points are recorded with a resolution of 1 nm in the range of 200-500 nm. HPMC samples are measured as 0.2 wt % aqueous solutions.

Molecular Weight Determination Via Water-Gel Permeation Chromatography

100 μL of a 0.1 wt % solution of the pertinent polysaccharide in water are separated via a HEMABio separation column with a corresponding precolumn. Measurement per static light scatter (miniDawn Treos, Wyatt Company) and the refraction index increment (OptilabRex, Wyatt Company) make possible the determination of absolute molecular weights.

$^1$H-NMR

The measurements were carried out on an FT-NMR spectrometer of the Bruker Ultraflex DRX200 type in DMSO-d6 at 100° C. Beforehand, the cellulose chains are degraded by the addition of a 10 vol % trifluoroacetic acid solution in water and heating at 50° C. for 3 h.

Materials:

The hydroxypropyl methylcellulose (HPMC) is purchased from Colorcon under the trade name Methocel®K15M Premium hydroxypropyl methylcellulose. The mass fraction is in the case of the hydroxypropylation 8.9 wt % and for the methylation 22.8 wt %. The determination of the molecular weight gives a bimodal distribution with the two maxima at $M_1$=134,000 g/mol and at $M_2$=282,000 g/mol. A 2 wt % solution in water gives a zero viscosity of 25 Pa·s and a pseudo-plasticity of 17.3. The turbidity point of this solution is 70.8° C.

2-Hydroxyethyl methylcellulose (HEMC) is Purchased from Aldrich.

For HEMC, the mass fraction in the case of the hydroxyethyl groups is 8.0 wt % and for the methylation 26.0 wt %. The determination of the molecular weight gives a bimodal distribution with the two maxima at $M_1$=156,000 g/mol and at $M_2$=464,000 g/mol. A 2 wt % solution in water gives a zero viscosity of 25 Pa·s and a pseudo-plasticity of 12.8. The turbidity point of this solution is 63.9° C.

4-(4-Decyloxybenzoyloxy)benzoic acid chloride is synthesized in accordance with the known literature (Barbera, L. Puig, P. Romero, J. L. Serrano, T. Sierra, Journal of the American Chemical Society, Vol. 128, 2006, 4487-4492, and A. K. Singh, S. Kumari, T. N. G. Row, J. Prakash, K. R. Kumar, B. Sridhar, T. R. Rao, Polyhedron, Vol. 27, 2008, 3710-3716).

Cholesteryl chloroformate (very pure; ≥99%; Fluka), octadecyl isocyanate (tech.; Aldrich) and octylchloroformate (97%; Aldrich) are used without further purification. All solvents are technically pure. DMSO was dried under an argon atmosphere via a molecular sieve 4 Å.

Molecular Weight Determination

The molecular weight was determined as below, if the molecular weight is not already known as a result of manufacturer's data. The determination of the molecular weight distribution was carried out via a GPC-MALS system that consists of the following components:

| | |
|---|---|
| Pump | Agilent 1200 series, consisting of degasser, pump, and autosampler; |
| Column | Precolumn HEMA Bio 300 + HEMA Bio 300, MZ analysis technology |
| MALS detector | miniDawn Treos; Wyatt; 3 angle |
| RI detector | Optilab-Rex; Wyatt; |
| Developing solvent | Millipore-water with addition of 100 mM NaNO$_3$, 500 ppm NaN$_3$. The refractive index increment (dn/dc) with the value 0.15 was taken from the data bank of Wyatt.eu. |

The cellulose ethers were dissolved with a mass concentration of 0.1% in the developing solvent and 100 μL of this solution were injected into the column. The evaluation of the measurement signals was carried out by means of the Astray software from the Wyatt Company. The evaluation of the light scatter signal was based on the Zimm model.

The invention claimed is:

1. A modified polysaccharide ether having a weight-averaged molecular weight of 40,000-500,000 g/mol, a zero-shear viscosity of more than 10 Pa·s, and a pseudo-plasticity of more than 20, the modified polysaccharide ether obtainable by reaction-of a polysaccharide ether (s) selected from the group consisting of hydroxypropyl methylcellulose (HPMC), hydroxyethyl methylcellulose (HEMC), methylcellulose, cellulose ethers with methyl and/or ethyl and/or propyl groups, and mixtures thereof with at least one cholesterol or cholesterol derivative, wherein the degree of substitution of cholesterol or cholesterol derivative groups is 0.001-0.01 per anhydroglucose unit and wherein the modified polysaccharide ether forms fringe micelles in aqueous solution.

2. The modified polysaccharide ether according to claim 1, wherein the polysaccharide ether is hydroxypropyl methylcellulose (HPMC) and a degree of substitution of the hydroxypropyl methylcellulose (HPMC), defined as a number of substituents per anhydrousglucose unit for methyl substituents, is between 0.8 and 2.2 and for hydroxypropyl substituents between 0.05 and 1.

3. The modified polysaccharide ether according to claim 1, wherein the polysaccharide ether is hydroxyethyl methyl cellulose (HEMC) and a degree of substitution of the hydroxyethyl methyl cellulose (HEMC), defined as a number of substituents per anhydrousglucose unit for methyl substituents, is between 0.8 and 2.2 and for hydroxyethyl substituents between 0.05 and 1.

4. The modified polysaccharide ether according to claim 1, wherein the cholesterol or cholesterol derivative is bound to a polymer chain directly or via an intermediate group.

5. The modified polysaccharide ether according to claim 1, wherein a cholesterol, cholesterol radical, or its derivative is bound to the polysaccharide ether as a carboxylic acid ester or a derivatized carboxylic acid ester.

6. The modified polysaccharide ether according to claim 1, wherein the modified polysaccharide ether obtainable by reaction of a polysaccharide ether with at least one cholesterol or cholesterol derivative is further modified by a modifying side group.

7. The modified polysaccharide ether according to claim 6, wherein the modifying side group is a reactive dye.

8. The modified polysaccharide ether according to claim 6, wherein the modifying side group is a reactive fluorescein derivative.

9. The modified polysaccharide ether according to claim 1, wherein the modified polysaccharide ether has a polyelectrolyte character.

10. A viscoelastic preparation comprising:
0.05-5 wt % of a modified polysaccharide ether in aqueous solution; the modified polysaccharide ether having a weight-averaged molecular weight of 40,000-500,000 g/mol, a zero-shear viscosity of more than 100 Pa·s, and a pseudo-plasticity of more than 20, wherein the modified polysaccharide ether is obtainable by reaction of a polysaccharide ether selected from the group consisting of hydroxypropyl methylcellulose (HPMC), hydroxyethyl methylcellulose (HEMC), methylcellulose, cellulose ethers with methyl and/or ethyl and/or propyl groups, and mixtures thereof with at least one cholesterol or cholesterol derivative, wherein the degree of substitution of cholesterol or cholesterol derivative groups is 0.001-0.01 per anhydroglucose unit.

11. A method for production of a viscoelastic preparation, the method comprising:
dissolving or dispersing a polysaccharide ether selected from the group consisting of hydroxypropyl methylcellulose (HPMC), hydroxyethyl methylcellulose (HEMC), methylcellulose, cellulose ethers with methyl and/or ethyl and/or propyl groups, and mixtures thereof in a solvent;
reacting the dissolved or dispersed polysaccharide ether with at least one cholesterol compound or cholesterol derivative to obtain a modified polysaccharide ether, the modified polysaccharide ether having a weight-averaged molecular weight of 40,000-500,000 g/mol, a zero-shear viscosity of more than 100 Pa·s, a pseudo-plasticity of more than 20 and wherein the degree of substitution of cholesterol or cholesterol derivative groups is 0.001-0.01 per anhydroglucose unit;
isolating the modified polysaccharide ether obtained;
separating low-molecular weight fractions;
dissolving in water to obtain the viscoelastic preparation; and packing and sterilizing the viscoelastic preparation.

12. The method according to claim 11, wherein the modified polysaccharide ether is dispersed above dissolution temperature in hot water and converted into a solution by cooling for production of aqueous solutions.

13. The method according to claim 11, wherein the modified polysaccharide ether forms fringe micelles in aqueous solution.

14. The viscoelastic preparation according to claim 10, wherein the modified polysaccharide ether forms fringe micelles in aqueous solution.

15. The viscoelastic preparation according to claim 10, wherein the polysaccharide ether is hydroxypropyl methylcellulose (HPMC) and a degree of substitution of the hydroxypropyl methylcellulose (HPMC), defined as a number of substituents per anhydrousglucose unit for methyl substituents, is between 0.8 and 2.2 and for hydroxypropyl substituents between 0.05 and 1.

16. The viscoelastic preparation according to claim 10, wherein the polysaccharide ether is hydroxyethyl methyl cellulose (HEMC) and a degree of substitution of the hydroxyethyl methyl cellulose (HEMC), defined as a number of substituents per anhydroglucose unit for methyl substituents, is between 0.8 and 2.2 and for hydroxyethyl substituents between 0.05 and 1.

17. The viscoelastic preparation according to claim 10, wherein a cholesterol, cholesterol radical, or its derivative is bound to the polysaccharide ether as a carboxylic acid ester or a derivatized carboxylic acid ester.

18. The viscoelastic preparation according to claim 10, wherein the modified polysaccharide ether obtainable by reaction of a polysaccharide ether with at least one cholesterol or cholesterol derivative is further modified by a modifying side group.

19. The viscoelastic preparation according to claim 10, wherein the modifying side group is a reactive dye or a reactive fluorescein derivative.

20. The viscoelastic preparation according to claim 10, wherein the modified polysaccharide ether has a polyelectrolyte character.

* * * * *